United States Patent
Brockbank

(10) Patent No.: US 11,930,809 B2
(45) Date of Patent: Mar. 19, 2024

(54) PRESERVATION OF BIOMATERIAL PROPERTIES AND METHODS OF STORING

(71) Applicant: LIFELINE SCIENTIFIC, INC., Itasca, IL (US)

(72) Inventor: Kelvin G. M. Brockbank, Charleston, SC (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 151 days.

(21) Appl. No.: 16/868,786

(22) Filed: May 7, 2020

(65) Prior Publication Data

US 2020/0260720 A1 Aug. 20, 2020

Related U.S. Application Data

(62) Division of application No. 14/057,521, filed on Oct. 18, 2013, now abandoned.

(60) Provisional application No. 61/715,576, filed on Oct. 18, 2012.

(51) Int. Cl.
*A01N 1/02* (2006.01)
*C12N 5/077* (2010.01)

(52) U.S. Cl.
CPC .......... *A01N 1/0226* (2013.01); *C12N 5/0655* (2013.01)

(58) Field of Classification Search
CPC ........................ A01N 1/0226; C12N 5/0655
See application file for complete search history.

(56) References Cited

U.S. PATENT DOCUMENTS

| 2009/0318342 A1 | 12/2009 | Nagase et al. |
| 2012/0177615 A1 | 7/2012 | Cook et al. |

FOREIGN PATENT DOCUMENTS

| EP | 0550760 A1 | 7/1993 | |
| JP | H05199868 A | 8/1993 | |
| JP | H0662843 A | 3/1994 | |
| JP | 2005-514435 A | 5/2005 | |
| WO | 99-03979 A1 | 1/1999 | |
| WO | 03-059296 A2 | 7/2003 | |
| WO | WO-2012097190 A2 * | 7/2012 | ............... A01N 1/02 |

OTHER PUBLICATIONS

Kim et al. Functional Viability of Chondrocytes Stored at 4° C. Tissue Engineering. 1996;2(1):75-81.*
Apr. 21, 2015 International Preliminary Report on Patentability issued in International Application No. PCT/US2013/065666.
May 31, 2016 Office Action issued in Chinese Patent Application No. 201380063773.8.
Dec. 16, 2016 Office Action issued in European Patent Application No. 13 786 792.5.
Fishbein, Kenneth et al. "Optimal Methods for the Preservation of Cartilage Samples in MRI and Correlative Biochemical Studies." Magnetic Resonance in Medicine. vol. 57, pp. 866-873, 2007.
Chen, Hongshu. "Application of Low Temperature Technique in Medical Science." China Science and Technology Press. pp. 21-24.
Kenji Onuma et al., "Cold preservation of rat osteochondral tissues in two types of solid organ preservation solution, culture medium and saline," Cell Tissue Banks (2009), 10:1-9.
Lawrence J. Bonassar et al., "Activation and Inhibition of Endogenous Matrix Metalloproteinases in Articular Cartilage: Effects on Composition and Biophysical Properties," Archives of Biochemistry and Biophysics, vol. 333, No. 2, Sep. 15, 1996, pp. 359-367.
Virginie Defamie et al., "Matrix Metalloproteinase Inhibition Protects Rat Livers from Prolonged Cold Ischemia—Warm Reperfusion Injury," Hepatology, vol. 47, No. 1, Jan. 2008, pp. 177-185.
Gundumi Aravinda Upadhya et al., "Glutathione, Lactobionate, and Histidine: Cryptic Inhibitors of Matrix Metalloproteinases Contained in University of Wisconsin and Histidine/Tryptophan/Ketoglutarate Liver Preservation Solutions," Hepatology, vol. 31, No. 5, May 2000, pp. 1115-1122.
Eric H. Karran et al., "In vivo model of cartilage degradation—effects of a matrix metalloproteinase inhibitor," Annals of the Rheumatic Disease, 1195, 54, pp. 662-669.
Sep. 12, 2017 Office Action issued in Japan Application No. 2015-538057.
Apr. 14, 2017 Chinese Office Action issued in Application No. 201380063773.8.
Jan. 5, 2018 Office Action issued in Chinese Application No. 201380063773.8.
Feb. 14, 2018 Office Action issued in Australian Patent Application No. 2017203616.
M. Yadegari et al. "Combination Effects of Prednisolone and Interleukin-4 Protect Bovine Nasal Cartilage Explants from Interleukin-1? Induced Degradation." Iranian Biomedical Journal. vol. 15, No. 4, Oct. 2011, pp. 143-150.
M. Benjamin et al. "Matrix Metalloproteinase Inhibitors as Investigative Tools in Pathogenesis and Management of Vascular Disease." Experientia Supplementum (2012). National Institute of Health. No. 103, Jan. 2013, pp. 209-279.
Cole et al. Doxycycline disrupts chondrocyte differentiation and inhibits cartilage matrix degradation. Arthritis & Rheumatism. 1994;12:1727-1734.
Nagase et al. Aggrecanases and cartilage matrix degradation. Arthritis Research & Therapy. 2003;5(2):94-103.
Smith et al. Oral administration of doxycycline reduces collagenase and gelatinase activities in extracts of human osteoarthritic cartilage. J Rheumatol. 1998;25(3):532-5.

(Continued)

*Primary Examiner* — Lynn Y Fan
(74) *Attorney, Agent, or Firm* — Oliff PLC

(57) ABSTRACT

Described herein are enhanced compositions and methods for storing biomaterials. In certain aspects, these biomaterials include natural and engineered eukaryotic tissues. The methods described herein include storing these biomaterials in such a manner that reduces or prevents the loss of biomaterial properties (e.g., extracellular matrix integrity, cell viability, or a combination thereof) occurring either during storage or after removal of the biomaterial from storage. In certain aspects, these biomaterials will be stored in animal product-free solutions containing an agent that prevents or reduces the loss of extracellular matrix integrity.

10 Claims, 6 Drawing Sheets

(56) References Cited

OTHER PUBLICATIONS

Whittaker, M. et al., "Matrix metalloproteinases and their inhibitors—current status and future challenges," Celltransmissions, vol. 17, No. 1, p. 3-14.

Wang, N. et al., "Up-regulation of TIMP-1 by genipin inhibits MMP-2 activities and suppresses the metastatic potential of human hepatocellular carcinoma," 17 pages.

Muehlbacher, F. et al., "Preservation solutions for transplantation," Transplantation Proceedings, 1999, p. 2069-2070, vol. 31, Elsevier Science Inc., New York, NY.

Bian, L. et al., "Mechanical and biochemical characterization of cartilage explants in serum-free culture," Journal of Biomechanics, 2008, p. 1153-1159, vol. 41, Pergamon Press. New York, NY.

Teng, M.S. et al., "Enhancing osteochondral allograft viability: Effects of storage media composition," Clinical Orthopaedics and Related Research, May 2008, p. 1804-1809, vol. 466.

Brockbank, K. G. M. et al., "Vitrification of porcine articular cartilage," Cryobiology, Apr. 2010, p. 217-221, vol. 60, Academic Press Inc.

Annabi, B. et al., "A PSP94-derived peptide PCK3145 inhibits MMP-9 secretion and triggers CD44 cell surface shedding: Implication in tumor metastasis," Clinical & Experimental Metastasis, Sep. 2005, p. 429-439, vol. 22.

Coussens, L. M. et al., "Matrix metalloproteinase inhibitors and cancer: trials and tribulations," Science, Mar. 29, 2002, p. 2387-2392, vol. 295, www.sciencemag.org.

Yamanaka, M. et al., "Sphingosine kinase 1 (SPHKI) is induced by transforming growth factor-0 and mediates TIMP-I up-regulation," Journal of Biological Chemistry, Dec. 2004, vol. 279, No. 52, p. 53994-54001.

Mar. 11, 2014 International Search Report and Written Opinion issued in PCT Application No. PCT/US2013/065666.

Brockbank et al. Tissue preservation. Advances in Biopreservation. 2006; 157-196.

Sep. 14, 2021 Office Action issued in Chinese Patent Application No. 201910748332.0.

Feb. 20, 2021 Office Action issued in Chinese Patent Application No. 201910748332.0.

\* cited by examiner

PRESERVATION OF BIOMATERIAL PROPERTIES AND METHODS OF STORING

CROSS-REFERENCE TO RELATED APPLICATION

This is a Division of application Ser. No. 14/057,521 filed Oct. 18, 2013, which claims the benefit of U.S. Provisional Application No. 61/715,576 filed Oct. 18, 2012. The disclosure of the prior application is hereby incorporated by reference in its entirety.

TECHNICAL FIELD

This disclosure relates to methods for storing eukaryotic biomaterials (e.g., cells in association with materials and tissues) while reducing or preventing the loss of biomaterial properties associated with storage. This disclosure further relates to maintaining biomaterial (i) extracellular matrix integrity, including extracellular matrix permeability, water content, and glycosaminoglycan content, and (ii) cell viability during storage.

BACKGROUND

Over the past few decades, storage methods and techniques have been developed to preserve eukaryotic tissues and cells. These storage methods and techniques are directed to storing various eukaryotic cells in engineered extracellular matrices, engineered tissues, and natural tissues for a period of time in a manner that allows for the use of these stored tissues at a later date, such as for implantation or transplantation into patients or for drug or chemical screening bioassays.

Although these storage methods and techniques are widely applicable both in basic research and translational research settings, maintaining biomaterial properties (e.g., extracellular matrix integrity and cell viability) during storage remains a challenge. For example, significantly decreased extracellular matrix permeability and tissue cell viability has been observed using current techniques, and these decreases can lead to inefficient biomaterial function after removal from storage.

In one example, chondrocytes and cartilage tissue are preserved using various storage techniques, and are subsequently removed from storage and used as osteochondral allografts. The allografts can repair (1) trauma-induced cartilage defects and (2) cartilage surfaces damaged by osteoarthritis. Use of chondrocytes and cartilage as osteochondral allografts to treat osteoarthritis is important because it is estimated that osteoarthritis currently affects about 20 million people in the United States. Thus, as a result, a large industry has grown to provide orthopedic implants to treat people with defective joints, osteoporotic fractures, or back problems resulting from a loss of endogenous cartilage or resulting from the damage of endogenous cartilage.

Although osteochondral allografts show promise for treating cartilage-related medical conditions, chondrocyte viability and extracellular matrix integrity of transplanted articular cartilage largely determines the outcome (i.e., a successful surgical outcome versus a failed surgical outcome, etc.) of osteochondral allograft transplantation. Current preservation techniques do not acceptably maintain extracellular matrix integrity of cartilage, and in certain aspects, chondrocyte viability could be improved. For example, conventional cryopreservation of chondrocytes and cartilage includes freezing these cells and tissues in a solution that includes dimethyl sulfoxide (DMSO), but these techniques result in death of 80-100% of the chondrocytes in articular cartilage plus extracellular matrix damage due to ice formation.

The poor cryopreservation results discussed above ultimately led to the practice of transplanting so-called "fresh" articular segments (i.e., chondrocytes and/or cartilage allografts). For example, donor-derived osteochondral tissue grafts are typically harvested within 24 hours of donor death and banked at 4° C. for up to 42 days for repair of clinical cartilage defects. In addition, commercially available fresh osteoarticular allografts are stored for at least 17 days to allow serologic and microbiologic testing prior to implantation to minimize potential infection in the recipient.

SUMMARY

Although osteochondral allograft transplantation has been an effective treatment for repairing (1) trauma-induced cartilage defects and (2) cartilage surfaces damaged by osteoarthritis, numerous challenges still exist for maintaining chondrocyte viability and extracellular matrix integrity of cartilage during storage. As demonstrated by recent research, it may be important to maintain both chondrocyte viability and extracellular matrix integrity to promote successful allograft transplantation. For example, if either cell viability and/or matrix integrity decreases during or after the removal from storage, the likelihood of a successful transplantation may decrease. These challenges exist with most eukaryotic cells in either engineered or natural tissues. Thus, new eukaryotic tissue and cell preservation techniques would be useful.

Described herein are compositions and methods for storing biomaterials. In certain aspects, these biomaterials include eukaryotic cells and eukaryotic tissues, such as chondrocytes and cartilage. The methods described herein include storing these biomaterials in a manner that reduces or prevents the loss of biomaterial properties, such as extracellular matrix permeability and chondrocyte viability, occurring either during storage or after removal of the biomaterials from storage. In certain aspects, these biomaterials are placed into a solution, which may include animal-derived products, and are subsequently stored for later use. In certain aspects, the solutions described herein contain an agent that prevents or reduces the loss of biomaterial properties, and in certain aspects, this agent can include an inhibitor of at least one enzyme. For example, this agent can include a natural or synthetic matrix metalloproteinase (MMP) inhibitor, which can include but is not limited to endogenous tissue inhibitors of metalloproteinase (TIMPs), compounds that regulate TIMP synthesis, or doxycycline, respectively.

The advantages of this disclosure will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

As shown in FIG. 2, the correlation coefficient increased from 0.78 to 0.90 during 4 days of post-storage recovery tissue culture.

DETAILED DESCRIPTION OF THE EMBODIMENTS

Figure 1:
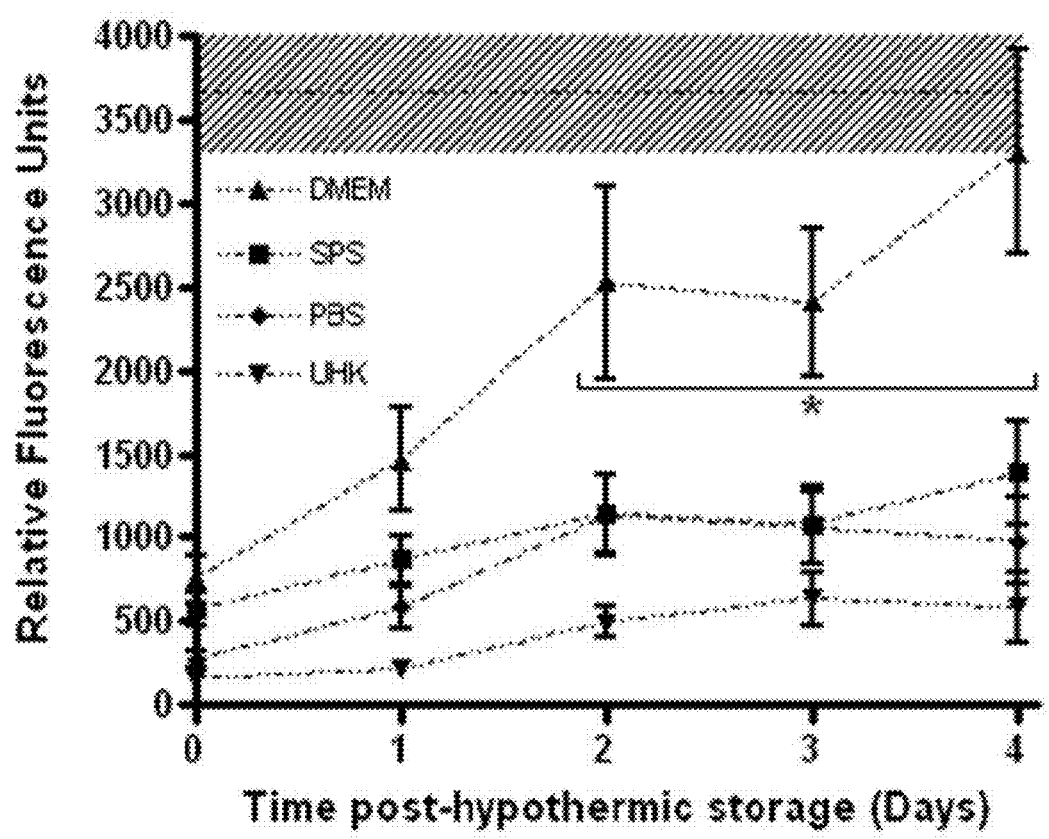
FIG. 1 is a graph comparing chondrocyte viability and proliferation after chondrocytes were stored for 28 days in four different solutions. Viability and proliferation were quantified by measuring relative fluorescence units (RFUs) of each sample.

The disclosed methods and compositions may be understood more readily by reference to the following detailed description of particular embodiments, the Examples included herein, and to the Figures and their descriptions. The aspects described below are not limited to specific compositions and/or methods as described which may, of course, vary.

Throughout this application, various publications are referenced. The disclosures of these publications in their entireties, as well as the publications included in the reference list below, are hereby incorporated by reference into this application to more fully describe the state of the art to which this disclosure pertains. The references disclosed are also individually and specifically incorporated by reference herein for the specific portions that are referenced.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or maximum. Furthermore, such an interpretation should apply regardless of the breadth of the range or the characteristics being described.

In this specification and in the claims that follow, reference will be made to a number of terms that shall be defined to have the following meanings:

"Animal product-free" solution includes a solution that does not include any animal product(s) or any products derived from animals excluding the biomaterial described further below. "Animal products" can include fetal bovine serum (FBS), which is an animal-derived product that includes growth factors and is often used in conventional cell culture. Thus, in one example, an "animal product-free" solution can include a solution lacking FBS.

The term "biomaterial" includes non-plant, mammalian eukaryotic cells and tissues.

Described herein are viable biomaterials and methods for storing such biomaterials. In certain aspects, these biomaterials include eukaryotic cells in both engineered and natural tissues, and the methods described herein include storing these biomaterials in such a manner that either reduces or prevents the loss of biomaterial properties (e.g., reducing or preventing loss of extracellular matrix integrity, tissue cell viability, or a combination thereof) occurring either during storage or after removal of the biomaterial from storage. In certain aspects, these biomaterials are placed into a solution, which can include an animal product-free solution, containing at least one agent that reduces or prevents a loss of biomaterial properties. Subsequently, the biomaterials placed into the solution containing at least one agent are then stored at a particular temperature range until these biomaterials are further needed. The concentration of the at least one agent is optimized such that biomaterial properties (e.g., extracellular matrix integrity and cell viability) are maximized.

In certain aspects, the biomaterials can include any non-plant, mammalian eukaryotic cells and/or tissues including primary cells (e.g., non-immortalized cells and/or tissues) and immortalized cells. In certain aspects, the biomaterials can include natural and engineered tissues and cells. Examples of natural and engineered biomaterials can include, but are not limited to, chondrocytes, cartilage, osteoblasts, osteoclasts, bone, tissue plugs, allograft tissue plugs, cartilage tissue plugs, a cornea, heart valves, blood vessels, a ureter, intestine, skin, teeth, tumor biopsies, intervertebral discs or bodies, ligaments, tendons, etc. In at least one aspect, the biomaterials include at least chondrocytes, cartilage, or a combination thereof. In other aspects, the biomaterials only include chondrocytes, cartilage, or a combination thereof. In certain aspects, the biomaterials include autograft tissues, allograft tissues, and xenograft tissues. For example, with regard to suitable human graft tissues, the allograft tissues and/or tissue plugs can be derived from a human donor. Xenograft tissues can be derived from a porcine donor, a bovine donor, an ovine donor, an equine donor, or any other species for medical purposes. The tissues described herein may also be derived from animal species for veterinary applications within the same species; examples include dogs, cats, sheep, cows, and horses.

When using the tissues and cells described herein with the compositions and methods described herein, one objective is to prevent loss of extracellular matrix integrity and/or reduce or prevent the loss of cell viability. For example, extracellular matrix integrity can be determined based on extracellular membrane permeability, extracellular membrane water content, extracellular membrane glycosaminoglycan content, or a combination thereof. In certain aspects, one objective is to maintain at least one of extracellular membrane permeability, extracellular membrane water content, extracellular membrane glycosaminoglycan content, or any combination thereof while storing the biomaterial to prevent or reduce loss of extracellular matrix integrity. When determining matrix integrity of the biomaterial, numerous techniques known in the art can be used. These techniques include matrix electrical conductivity assays that measure permeability, water content, and glycosaminoglycan content, indentation tests, stress/strain tests, elasticity, RAMAN spectroscopy, various microscopic methods (such as laser scanning microscopy with second harmonic generation), etc. As further stated above, another objective is to reduce or prevent the loss of the biomaterial's cell viability. In certain aspects, various types of cell death, including but not limited to, necrotic cell death, apoptotic cell death, autophagic (Type II) cell death, anoikis, and necroptosis can be reduced or prevented using the compositions and methods described herein, and in certain aspects, these types of cell death can be limited by the use of an agent as described further below. In addition, metabolic activity assays (e.g., a resazurin assay), various cellular staining techniques (e.g., a Trypan Blue exclusion assay and live/dead stains), immunohistochemistry, biochemistry and various gene expression assays can be used.

In one aspect and when tissues containing a matrix are being used as a biomaterial, preventing or reducing the loss of extracellular matrix integrity and loss of cell viability is important to maintain structural integrity and normal biological function of the tissue. For example, cartilage contains chondrocytes (i.e., cells) and an extracellular matrix, wherein the extracellular matrix is primarily composed of collagen fibers, proteoglycans, and elastin fibers. Both chondrocyte viability and cartilage extracellular matrix integrity are important to maintain normal, physiological biological function in in vivo, ex vivo, and in vitro applications. For example, the extracellular matrix of cartilage provides structural integrity and maintains a certain level of rigidity in vivo, which functions in bone support, proper joint mobility, etc. In certain aspects, the permeability of the cartilage's extracellular matrix is of particular importance. For example, cartilage permeability can be associated with and may play an important role in maintaining the structural integrity of the cartilage's extracellular matrix and aiding to maintain chondrocyte viability as well. In certain aspects, decreased permeability of the cartilage's extracellular matrix can be associated with increased chondrocyte viability and decreased cartilage extracellular matrix structural integrity. This increased viability and decreased structural integrity due to production of cell products, such as enzymes, can lead to a decreased likelihood of successful transplantation when the stored cartilage is being subsequently used for allograft transplantation. Thus, in certain aspects, the methods and compositions described herein are used to prevent or reduce the loss of cartilage extracellular matrix integrity while reducing and/or preventing the loss of chondrocyte viability, and in certain aspects, the methods and compositions described herein are used to reduce and/or prevent the loss of cartilage extracellular matrix integrity in an allograft while optimizing chondrocyte viability.

The biomaterials described herein can be placed into a solution that prevents or reduces the loss of biomaterial properties (e.g., extracellular matrix integrity, cell viability, or a combination thereof), and in certain aspects, this solution can be either an animal product-free solution (e.g., excludes FBS) or can contain animal products (e.g., includes FBS). It should be noted that the below descriptions and embodiments also apply to solutions containing animal products including the biomaterial. In certain aspects, the biomaterial is at least partially submerged in the solution, and in other aspects, the biomaterial is completely submerged in the solution.

In one aspect, the solution can be an extracellular-type solution including at least one agent that prevents or reduces the loss of biomaterial properties (e.g., extracellular matrix integrity, cell viability, or a combination thereof). For example, extracellular-type solutions can include isotonic, plasma-like solutions with ion complements that mimic the normal extracellular environment of cells and tissues. These isotonic, plasma-like solutions can include cell culture medium, which provide various amino acids and metabolites to the biomaterial (e.g., cells and/or tissues) for nutritional support. For example, cell culture medium used for the extracellular-type solution can include, but are not limited to, Dulbecco's Modified Eagle Medium (DMEM), αMEM, Glasgow's MEM, Ham's F10, Ham's F-12, Leibovitz's L-15, Iscove's Modified DMEM, DMEM/Ham's F-12, and derivatives thereof. The extracellular-type solution can be animal product-free, such that, before placing the biomaterial into the cell solution, the cell solution contains no animal products. For example, when using cell culture medium, the cell culture medium would not contain fetal bovine serum (FBS) or any other product derived from an animal.

In certain aspects, the solution includes an intracellular-type solution. The intracellular-type solution can include, but is not limited to, an isotonic solution formulated to restrict the passive exchange of water and ions between cells in the biomaterial and intracellular-type solution during storage. For example, an intracellular-type solution can include a non-permeating anion such as lactobionate or gluconate to partially replace chloride ions in the extracellular space, which provides osmotic support to balance the intracellular oncotic pressure generated by cytosolic macromolecules and their associated counter-ions locked inside the cell. Intracellular-type solutions can include, but are not limited to, VIASPAN® (i.e., Belzer's Solution) and UNISOL® (e.g., SPS-1). Similar to the extracellular-type solution described above, the intracellular-type solution can be animal product-free.

Additional components can be added to the intracellular-type solution to further supplement the intracellular-type solution and to further promote biomaterial viability. For example, these additional components provide additional nutritional support for the biomaterial, which reduces or prevents the loss of viability of the biomaterial. These additional components can include, but are not limited to, a nutrient cocktail having non-animal derived (i.e., synthetically derived) essential amino acids, synthetically derived non-essential amino acids, synthetically derived vitamins, synthetically derived lipids, synthetically derived carbohydrates, or any combination thereof. Examples of the carbohydrates included in the nutrient cocktail can further include monosaccharides (e.g., glucose, fructose, galactose), disaccharides (e.g., maltose, lactose, etc.), or a combination thereof. Examples of amino acids provided in the cocktail can include, but are not limited to, any combination of glycine, L-arginine, L-cystine, L-glutamine, L-histidine, L-isoleucine, L-leucine, L-lysine, L-methionine, L-phenylalanine, L-serine, L-threonine, L-tryptophan, L-tyrosine, L-valine, or any salt thereof. Examples of vitamins provided in the cocktail can include, but are not limited to, any combination of choline, D-calcium, folic acid, niacinamide, pyridoxine, riboflavin, thiamine, inositol, or any salt thereof.

As indicated above, an agent that prevents or reduces the loss of biomaterial properties (e.g., extracellular matrix integrity, cell viability, or a combination thereof) can be included in the solution. In certain aspects, the agent can prevent or reduce the loss of extracellular matrix integrity. For example, agents that prevent or reduce the loss of extracellular matrix integrity can include small organic compounds, inorganic compounds, biological molecules (e.g., proteins, polypeptides, peptides, nucleic acids, nucleic acid aptamers, peptide aptamers), or any combination thereof that inhibits or reduces the loss of extracellular matrix integrity in the solution when, for example, compared to a control. In certain aspects, the agent can reduce the loss of the biomaterial's properties (e.g., extracellular matrix integrity) by, for example, 5% or more, 10% or more, 20% or more, 30% or more, 40% or more, 50% or more, 60% or more, 70% or more, 80% or more, 90% or more, or 99% or more when compared to, for example, a control. Stated another way, the agent can substantially or completely inhibit the loss of a biomaterial's properties by, for example, at least 80%, at least 85%, at least 90%, at least 95%, at least 99%, or 100% when compared to, for example, a control. In certain aspects, the solution includes an agent at concentrations ranging from 1 pM to 1000 µM, 1 pM to 500 µM, 1 pM to 30 µM, 1 pM to 1000 nM, 1 pM to 500 nM, 1 pM to 250 nM, 100 pM to 750 µM, 100 pM to 500 µM, 100 pM to 20 µM, 100 pM to 1000 nM, 1 pM to 750 nM, 1 pM to 500 nM, 1 pM to 250 nM, 1 pM to 1 nM, 500 pM to 500 µM, 500 pM to 250 µM, 500 pM to 100 µM, 500 pM to 10 µM, 500 pM to 1000 nM, 500 pM, to 750 nM, 500 pM to 500 nM, 500 pM to 250 nM, 500 pM to 100 nM, 500 pM to 1 nM, 1 nM to 1000 µM, 1 nM to 750 µM 1 nM to 500 µM, 1 nM to 250 µM, 1 nM to 100 µM, 1 pM to 1 µM, 100 nM to 1000 µM, 100 nM to 750 µM, 100 nM to 500 µM, 100 nM to 250 µM, 100 nM to 100 µM, 100 pM to 1 µM, 250 nM to 1000 µM, 250 nM to 750 µM, 250 nM to 500 µM, 250 nM to 250 µM, 250 nM to 100 µM, 250 nM to 1 µM, 500 nM to 1000 µM, 500 nM to 750 µM, 500 nM to 500 µM, 500 nM to 250 µM, 100 nM to 100 µM, 500 nM to 1 µM, 750 nM to 1000 µM, 750 nM to 750 µM, 750 nM to 500 µM, 750 nM to 250 µM, 750 nM to 100 µM, 750 nM to 1 µM, 0.5 µM to 1000 µM, from 10 µM to 950 µM, from 20 µM to 900 µM, from 30 µM to 850 µM, from 40 µM, to 800 µM, from 50 µM to 750 µM, from 60 µM to 700 µM, from 70 µM to 650 µM, from 80 µM to 600 µM, from 90 µM to 550 µM, from 100 µM to 500 µM, from 110 µM to 450 µM, from 120 µM, to 400 µM, from 130 µM to 350 µM, from 140 µM to 300 µM, from 150 µM to 250 µM, from 160 µM to 200 µM, from 0.5 µM to 100 µM, from 1 µM to 90 µM, from 5 µM to 90 µM, from 10 µM to 85 µM, from 10 µM to 75 µM, from 20 µM to 85 µM, from 20 µM to 65 µM, from 30 µM to 70 µM, from 30 to 50 µM, from 40 µM to 80 µM, or from 40 µM to 50 µM, wherein any concentration occurring within the above ranges can also serve as an endpoint for a range.

In one aspect, it is believed that the agent inhibits or reduces the activity of an enzyme that affects the biomaterial's properties (e.g., extracellular matrix integrity). Thus, the agent can act as an enzyme inhibitor of a specific enzyme associated with promoting damage of the biomaterial (e.g., extracellular matrix damage). In this aspect, the enzyme inhibitor can be used in the ranges described above to inhibit or reduce the activity of an enzyme and to increase retention of biomaterial properties (e.g., retention of extracellular matrix integrity). In one aspect, this enzyme inhibitor can specifically include but is not limited, to a matrix metalloproteinase (MMP) inhibitor.

For example, in certain aspects MMPs can adversely affect biomaterial properties (e.g., extracellular matrix integrity) via enzymatic degradation of at least a portion of the biomaterial and potentially lead to inefficient biomaterial function after storage. Thus, in certain aspects, it is desired to reduce or inhibit MMP enzyme activity by using an MMP inhibitor. For example, the MMP inhibitor can inhibit or reduce the enzymatic activity of MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP26, MMP27, MMP28 or any combination thereof. In certain aspects, the MMP inhibitor reduces or inhibits the enzymatic activity of at least one of MMP1, MMP 8, MMP9, MMP13, or any combination thereof. In certain aspects, the MMP inhibitor reduces or inhibits the enzymatic activity of at least two of MMP1, MMP 8, MMP9, MMP13, or any combination thereof. In certain aspects, the MMP inhibitor reduces or inhibits the enzymatic activity of at least three of MMP1, MMP 8, MMP9, MMP13, or any combination thereof. Furthermore, the MMP inhibitor can include but is not limited to natural or synthetic matrix metalloproteinase (MMP) inhibitors. Synthetic MMP inhibitors generally contain a chelating group that tightly binds the catalytic zinc atom at an MMP's active site. Common chelating groups include hydroxamates, carboxylates, thiols, and phosphinyls. In certain aspects, hydroxymates are particularly potent inhibitors of MMPs due to their bidentate chelation of zinc atoms. Zinc chelators can include diethyldithiocarbamate (DEDTC) and calcium ethylenediaminetetraacetic acid (EDTA). In certain aspects, the inhibitors described herein can include, but are not limited to, doxycycline, PCK3145 (a synthetic peptide corresponding to amino acids 31-45 of prostate secretory protein 94), BB-2516 (Marimastat), BB-94 (i.e., batimastat, which is (2R,3S)—$N^4$-Hydroxy-N1-[(1S)-2-(methylamino)-2-oxo-1-(phenylmethyl)ethyl]-2-(2-methylpropyl)-3-[(2-thienylthio)methyl]butanediamide), compounds that regulate endogenous tissue inhibitors of metalloproteinase (TIMPs) (e.g., compounds that regulate TIMP synthesis), or any combination thereof. For example, genipin, a natural compound, has been shown to upregulate the expression of TIMP-1. Without wishing to be bound by theory, genipin induced upregulation of TIMP-1 reduces or inhibits MMP-2 activity, and in certain aspects, genipin can be used to inhibit or reduce MMP enzyme activity in the methods and compositions described herein. Furthermore, transforming growth factor-β (TGF-β) signaling has been shown to play a pivotal role in extracellular matrix deposition by stimulating collagen production and other extracellular matrix proteins and by inhibiting matrix degradation by up-regulation of the TIMP-1 gene. Therefore, compounds that regulate TGF-β signaling and ultimately regulate expression TIMP expression (e.g., TIMP-1 expression) and MMP inhibition may be used as an inhibitor with the methods described herein.

In certain aspects, the biomaterial is placed into a solution that includes at least one agent that reduces or prevents a loss of extracellular matrix integrity of the biomaterial and at least one or more additional agents that promote retention of cell viability.

After placing the biomaterial into any of the solutions described above, the biomaterial can then be stored. For example, after placing the biomaterial into the solution including at least one agent, this mixture can be stored at various temperatures to further promote preservation of the biomaterial's extracellular matrix and to further prevent or reduce a loss of viability of the biomaterial. For example, these temperatures can include, but are not limited to, hypothermic temperatures and normothermic temperatures. When storing the biomaterial in hypothermic temperatures, it is preferred to reduce or prevent ice nucleation. In certain aspects, hypothermic temperatures can include temperatures ranging −25° C. from to +35° C., ranging from −15° C. from to +30° C., ranging from −5° C. to +25° C., ranging from −5° C. to +20° C., ranging from −5° C. to +15° C., ranging from −5° C. to +10° C., ranging from −5° C. to +5° C., ranging from 0° C. to +10° C., ranging from 0° C. to +9° C., ranging from 0° C. to +8° C., ranging from 0° C. to +7° C., ranging from 0° C. to +6° C., ranging from 0° C. to +5° C., ranging from 0° C. to +5° C., ranging from 0° C. to +4° C., ranging from 0° C. to +3° C., ranging from 0° C. to +2° C., ranging from +1° C. to +8° C., ranging from +1° C. to +6° C., ranging from +1° C. to +4° C., ranging from +1° C. to +3° C., ranging from +2° C. to +9° C., ranging from +2° C. to +6° C., ranging from +2° C. to +4° C., ranging from +3° C. to +8° C., ranging from +3° C. to +6° C., ranging from +3° C. to +5° C., ranging from +4° C. to +8° C., ranging from +4° C. to +6° C., ranging from +5° C. to +9° C., ranging from +5° C. to +7° C., ranging from +6° C. to +10° C., ranging from +6° C. to +8° C., ranging from +7° C. to +9° C., and ranging from +8° C. to +10° C. In certain aspects and depending on the biomaterial, hypothermic temperatures may be preferred. For example, if chondrocytes and/or cartilage are the biomaterial, the chondrocytes and/or cartilage can be preserved using hypothermic temperatures described above. For example, if chondrocytes and/or cartilage are the biomaterial, hypothermic temperatures ranging preferably from −25° C. to +35° C., ranging more preferably from −5° C. from to +25° C., and most preferably 0° C. to +10° C. In certain aspects, the biomaterial can be stored for hours, days, months or years. For example, it may be preferable to store chondrocytes and/or cartilage (e.g., cartilage tissue plugs) from a few hours up to three months, from a few hours up to two months, from a few hours up to one month, etc.

In certain aspects, the animal product-free solution of the stored biomaterial can be replaced at various desired time intervals. For example, the animal product-free solution can be replaced twice weekly, one a week, every two weeks, once a month, once every two month, etc. throughout the duration of biomaterial storage and until the stored biomaterial is removed from storage for further use.

When using the methods and compositions described above, in certain aspects, the biomaterial includes chondrocytes and/or cartilage. One objective of this disclosure includes reducing or preventing the loss of extracellular matrix material properties and optimizing retention of cell viability of the biomaterial during storage for later use. In this aspect, the chondrocytes and/or cartilage are placed into a solution that includes at least one agent that at least reduces or prevents a loss of extracellular matrix integrity. The chondrocytes and/or cartilage can be placed into the extracellular-type solution, wherein the extracellular-type solution includes a MMP inhibitor at a concentration as described above, and this mixture can be subsequently stored at a hypothermic temperature ranging from −25° C. to +30° C. for a period of time. In another aspect, the chondrocytes and/or cartilage can be placed into the intracellular-type solution, wherein the intracellular-type solution includes a MMP inhibitor at a concentration as described above, and in certain aspects, this intracellular-type solution optionally further includes the nutrient cocktail described above to promote retention of cell viability. The chondrocytes and/or cartilage placed into the intracellular-type solution are subsequently stored at a hypothermic temperature ranging from −25° C. to +25° C. for a period of time.

In one aspect, it is desirable to determine which solution best reduces or prevents a loss of biomaterial properties (e.g., extracellular matrix integrity including extracellular matrix permeability, water content, cell viability, etc.) during storage. While further determining the methods and compositions that best reduce or prevent a loss of biomaterial properties identical biomaterials can be placed into two different solutions as described above (i.e., the intracellular-type and the extracellular-type). The two solutions will both contain an agent that reduces or prevents the loss of extracellular matrix properties of the biomaterial, and the intracellular-type solution can optionally contain a nutrient cocktail. After placing the identical biomaterials into the two different solutions, the biomaterials in the two different solutions will be stored in a similar manner (i.e., at the same temperature, for the same duration of time, etc.). After a period of time, the identical biomaterials that were placed in two different solutions can be removed from storage and biomaterial properties will be tested (e.g., cell viability, extracellular matrix permeability, etc.) and compared to determine which methods and compositions best reduce or prevent the loss of viability of the biomaterial. In certain aspects, these methods and techniques will be applied to chondrocytes and/or cartilage to further determine which solution best reduces or prevents a loss of biomaterial integrity during storage.

In some embodiments, the present disclosure relates to a composition comprising a biomaterial placed in a solution that includes at least one agent that reduces or prevents a loss of biomaterial properties. The biomaterial properties may comprise extracellular matrix integrity, cell viability, or a combination thereof. The extracellular matrix integrity may include, for example, extracellular matrix permeability, extracellular matrix water content, extracellular matrix glycosaminoglycan content, or any combination thereof. The biomaterial may include an eukaryotic tissue. In some embodiments, the biomaterial may comprise cartilage. In some embodiments, the biomaterial comprises chondrocytes in an extracellular matrix. In some embodiments, the biomaterial comprises an allograft material having viable cells. In some embodiments, the biomaterial may comprise an allograft material having viable cells and an extracellular matrix, and wherein the agent reduces or prevents the loss of extracellular matrix integrity, cell viability, or a combination thereof. In such embodiments, the allograft material may be cartilage. In embodiments, the solution may be an animal-product free solution, such as a solution that does not include fetal bovine serum. In some embodiments, the solution may be an extracellular-type solution, such as an isotonic extracellular-type isotonic. In some embodiments, the solution may be an intracellular-type solution, such as an isotonic intracellular-type solution.

In some embodiments, the at least one agent that reduces or prevents a loss of biomaterial properties is present in the solution at a concentration ranging from 100 pM to 1 mM. In some embodiments, the at least one agent is an enzyme inhibitor, such as an enzyme inhibitor that minimizes an enzymatic activity to reduce or prevent the loss of biomaterial properties, wherein the biomaterial properties include extracellular matrix integrity. For example, the enzyme inhibitor may inhibit at least one matrix metalloproteinase, such as one or more of MMP 1, MMP2, MMP3, MMP7, MMP8, MMP9, MMP10, MMP11, MMP12, MMP13, MMP14, MMP15, MMP16, MMP17, MMP 19, MMP 20, MMP 21, MMP 23A, MMP23B, MMP24, MMP25, MMP26, MMP27, MMP28 or any combination thereof. In some embodiments, the enzyme inhibitor may be present at a concentration in the solution ranging from 1.0 nM to 1000 µM. In some embodiments, the enzyme inhibitor may be selected from the group consisting of doxycycline, TIMPs, a compound that up-regulates endogenous TIMPs, PCK3145, BB-2516, and BB-94.

In some embodiments, the present disclosure relates to a composition comprising a biomaterial placed in a solution that includes at least one agent that reduces or prevents a loss of biomaterial properties, where the solution is an animal product-free solution that comprises an extracellular-type solution that is isotonic, wherein the biomaterial comprises chondrocytes in an extracellular matrix or cartilage, and wherein the at least one agent comprises an enzyme inhibitor of a matrix metalloproteinase having a concentration ranging from 1.0 nM to 1 mM. In some embodiments, the present disclosure relates to a composition comprising a biomaterial placed in a solution that includes at least one agent that reduces or prevents a loss of biomaterial properties, where the solution is an animal product-free solution that comprises an intracellular-type solution that is isotonic, wherein the biomaterial comprises chondrocytes in an extracellular matrix or cartilage, and wherein the at least one agent comprises an enzyme inhibitor of a matrix metalloproteinase having a concentration ranging from 1.0 nM to 1 mM.

In some embodiments, the present disclosure relates to a method for storing a biomaterial comprising placing the biomaterial in a solution that includes at least one agent that reduces or prevents a loss of biomaterial properties. In some embodiments, the biomaterial may comprise a natural or engineered eukaryotic tissue. In some embodiments, the biomaterial may comprise cartilage. In some embodiments, the biomaterial may comprise chondrocytes in an extracellular matrix. In some embodiments, the biomaterial may comprise an allograft material having viable cells. In some embodiments, the biomaterial may comprise an allograft material having viable cells and an intact extracellular matrix. In some embodiments, the allograft material may be cartilage. In some embodiments, the solution may be an animal product-free solution. In some embodiments, the solution may be an extracellular-type solution, such as an extracellular-type solution that is isotonic. In some embodiments, the solution may be an intracellular-type solution, such as an intracellular-type solution that is isotonic. In some embodiments, the solution does not include fetal bovine serum. In some embodiments, the at least one agent may be present in the solution at a concentration ranging from 1.0 nM to 1 mM. In some embodiments, the at least one agent may be an enzyme inhibitor, such as an enzyme inhibitor minimizes an enzymatic activity to reduce or prevent loss of biomaterial properties, wherein the biomaterial properties include extracellular matrix integrity. In some embodiments, the enzyme inhibitor may inhibit at least one matrix metalloproteinase, such as at least one matrix metalloproteinase selected from the group consisting of MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP26, MMP27, MMP28 and any combination thereof. In some embodiments, the enzyme inhibitor may be selected from the group consisting of doxycycline, TIMPs, a compound that up-regulates endogenous TIMPs, PCK3145, BB-2516, and BB-94. In some embodiments, the method may further comprise storing the biomaterial placed in the solution at a temperature ranging from −25° C. to +35° C. In some embodiments, the solution is an animal product-free solution that comprises an extracellular-type solution, wherein the extracellular-type solution is isotonic, wherein the biomaterial is chondrocytes in an extracellular matrix or cartilage, and wherein the at least one agent comprises an enzyme inhibitor of a matrix metalloproteinase having a concentration ranging from 1.0 nM to 1 mM. In some embodiments, the solution is an animal product-free solution that comprises an intracellular-type solution, wherein the intracellular-type solution is isotonic, wherein the biomaterial is chondrocytes in an extracellular matrix or cartilage, and wherein the at least one agent comprises an enzyme inhibitor of a matrix metalloproteinase having a concentration ranging from 1.0 nM to 1 mM.

In some embodiments, the present disclosure relates to a composition comprising an animal product-free solution, wherein the solution includes at least one matrix metalloproteinase inhibitor. In some embodiments, the animal product-free solution includes a cell culture media. In some embodiments, the animal product-free solution is an intracellular-type solution that does not include a cell culture media. In some embodiments, the matrix metalloproteinase inhibitor reduces or inhibits enzymatic activity of at least one of MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP26, MMP27, MMP28 or any combination thereof. In some embodiments, the at least one matrix metalloproteinase inhibitor reduces or inhibits enzymatic activity of at least one of MMP1, MMP8, MMP9, MMP13, or any combination thereof. In some embodiments, the at least one matrix metalloproteinase inhibitor reduces or inhibits enzymatic activity of at least two of MMP1, MMP8, MMP9, MMP13, or any combination thereof. In some embodiments, the at least one matrix metalloproteinase inhibitor reduces or inhibits enzymatic activity of at least three of MMP1, MMP8, MMP9, MMP13, or any combination thereof. In some embodiments, the at least one matrix metalloproteinase inhibitor is present in the animal-product free solution at concentrations ranging from 1.0 nM to 1000 µM. In some embodiments, the at least one matrix metalloproteinase inhibitor is present in the animal-product free solution at concentrations ranging from 100 nM to 100 µM. In some embodiments, the at least one matrix metalloproteinase inhibitor is present in the animal-product free solution at concentrations ranging from 1 pM to 30 µM. In some embodiments, the at least one matrix metalloproteinase inhibitor is present in the animal-product free solution at concentrations ranging from 100 pM to 20 µM. In some embodiments, the at least one matrix metalloproteinase inhibitor is present in the animal-product free solution at concentrations ranging from 500 pM to 10 µM. In some embodiments, the at least one matrix metalloproteinase inhibitor is present in the animal-product free solution at concentrations ranging from 1 µM to 5 µM. In some embodiments, the at least one matrix metalloproteinase inhibitor is selected from the group consisting of doxycycline, TIMPs, a compound that up-regulates endogenous TIMPs, PCK3145, BB-2516, and BB-94. In some embodiments, the at least one matrix metalloproteinase inhibitor is selected from the group consisting of doxycycline, TIMPs, a compound that up-regulates endogenous TIMPs, PCK3145, BB-2516, and BB-94. In some embodiments, the one matrix metalloproteinase inhibitor is doxycycline ranging from 1.0 nM to 1000 µM. In some embodiments, the intracellular-type solution further comprises a nutrient cocktail that includes at least one of the following components: D-glucose, glycine, L-arginine hydrochloride, L-cystine hydrochloride, L-glutamine, L-histidine hydrochloride, L-isoleucine, L-leucine, L-lysine hydrochloride, L-methionine, L-phenylalanine, L-serine, L-threonine, L-tryptophan, L-tyrosine, L-valine, choline, D-calcium pantothenate, folic acid, niacinamide, pyridoxine, riboflavin, thiamine, inositol, any salt thereof, or any combination thereof. In some embodiments, the intracellular-type solution further comprises a nutrient cocktail that includes at least one of the following components: D-glucose, glycine, L-arginine hydrochloride, L-cystine hydrochloride, L-glutamine, L-histidine hydrochloride, L-isoleucine, L-leucine, L-lysine hydrochloride, L-methionine, L-phenylalanine, L-serine, L-threonine, L-tryptophan, L-tyrosine, L-valine, choline, D-calcium pantothenate, folic acid, niacinamide, pyridoxine, riboflavin, thiamine, inositol, any salt thereof, or any combination thereof.

In some embodiments, the present disclosure relates to a composition comprising a biomaterial in a solution that promotes retention of extracellular matrix integrity and cell viability, wherein the solution includes an enzyme inhibitor. In some embodiments, the present disclosure relates to a method comprising storing a biomaterial at hypothermic temperatures in an intracellular-type solution with at least one additive that promotes retention of extracellular matrix integrity and cell viability. In some embodiments, the at least one additive comprises an enzyme inhibitor, an amino acid, a plurality of amino acids, a sugar, a plurality of sugars, a lipid, a plurality of lipids, a vitamin, a plurality of vitamins, or any combination thereof.

The foregoing is further illustrated by reference to the following examples, which are presented for purposes of illustration and are not intended to limit the scope of the present disclosure.

EXAMPLES

The following examples are put forth so as to provide those of ordinary skill in the art with a complete disclosure and description of how the compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but normal errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process.

Preliminary Research

Samples were hypothermically stored in various solutions (e.g., DMEM, SPS, PBS, and UHK) for 28 days. These samples were subsequently removed from storage and cartilage chondrocyte viability and permeability (i.e., the cartilage's extracellular matrix integrity) were evaluated. As shown in FIG. 1, chondrocyte viability and proliferation were evaluated in samples stored for 28 days in four different solutions. Cells stored in DMEM demonstrated considerably higher chondrocyte viability than the samples stored in SPS, PBS, and UHK as shown by assessing viability with the resazurin reduction metabolic assay. Specifically, the data of FIG. 1 is expressed as the mean RFU/6 mm plug±1 se and * indicates significant differences at p<0.05. Statistically significant differences in cell viability were observed between cells stored in DMEM and the other solutions starting at day 2. DMEM achieved control levels after 4 days in culture. Untreated control values are shown as the mean (dashed line)±1 se (hatched) at the top of the figure. The correlation coefficient ($R^2$) between these results and loss of cartilage matrix permeability (shown in FIG. 3) increased over 4 days in post-storage recovery tissue culture (FIG. 1). These data demonstrated that complex extracellular-type culture media (e.g., DMEM) are best for maintaining chondrocyte functions (FIG. 1), which correlates with cell survival (i.e., cell viability). Furthermore, storage of these samples for approximately one month in both intracellular-type solutions (i.e., SPS and UHK) resulted in less metabolic during post-recovery proliferation under physiologic tissue culture conditions (FIG. 1). Similarly, storage of these samples in phosphate buffered saline (PBS), an extracellular formulation without nutrients, also demonstrated less proliferation during post-recovery tissue culture. These observations suggest that nutrients are responsible for the significantly better performance (i.e., chondrocyte viability) of cartilage plugs stored in DMEM (FIG. 1).

Figure 2:
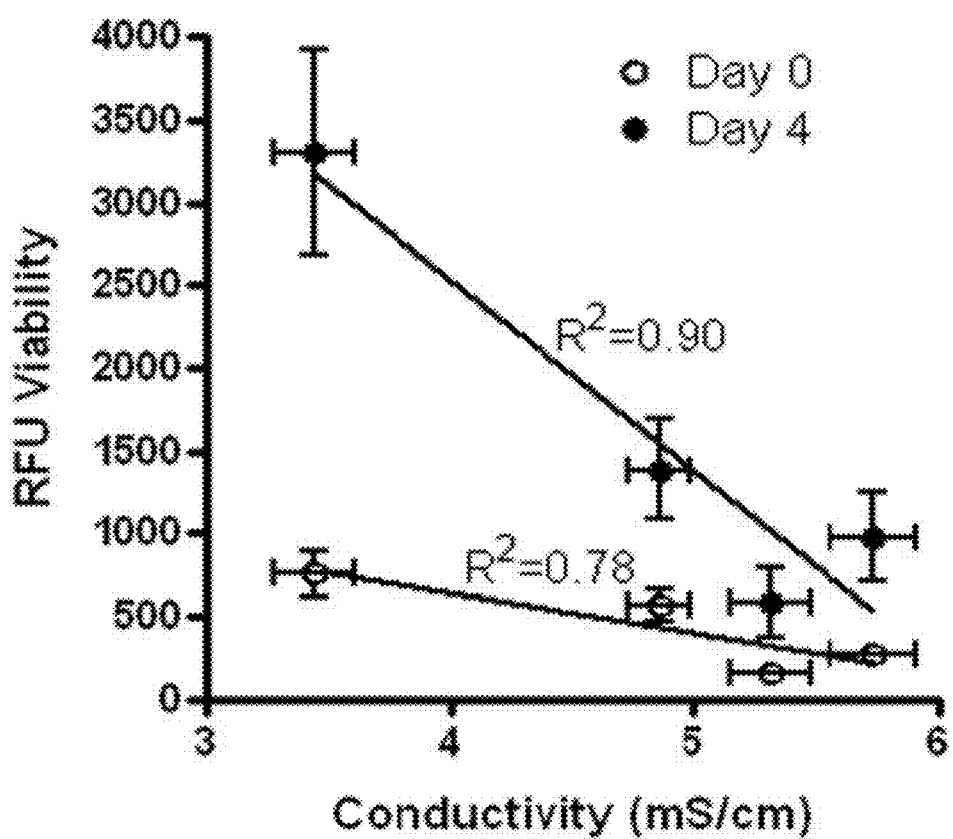
FIG. 2 is a graph showing the correlation coefficient ($R^2$) between high cell viability and loss of cartilage matrix permeability and conductivity occurring during cold storage in 4 different solutions.

Interestingly, cartilage stored in DMEM demonstrated the highest cell viability (i.e., RFU Viability values) but the lowest electrical conductivity (mS/cm) after 4 days of post-storage recovery. Although this result indicated that DMEM promoted the highest cell viability, this result also indicated that the greatest loss of cartilage matrix permeability occurred while cartilage was stored in DMEM. This observation led to the hypothesis that retention of cell viability resulted in release of cell-derived materials that impacted extracellular matrix permeability. Specifically, these studies demonstrated a strong correlation ($R^2$=0.90) between retention of cell viability and loss of cartilage matrix permeability (FIG. 2). FIG. 2 specifically shows the correlation coefficient ($R^2$) between high cell viability and loss of cartilage matrix permeability and conductivity, due to cold storage in 4 different solutions increased from 0.78 to 0.90 during 4 days of post-storage recovery tissue culture.

Figure 3:
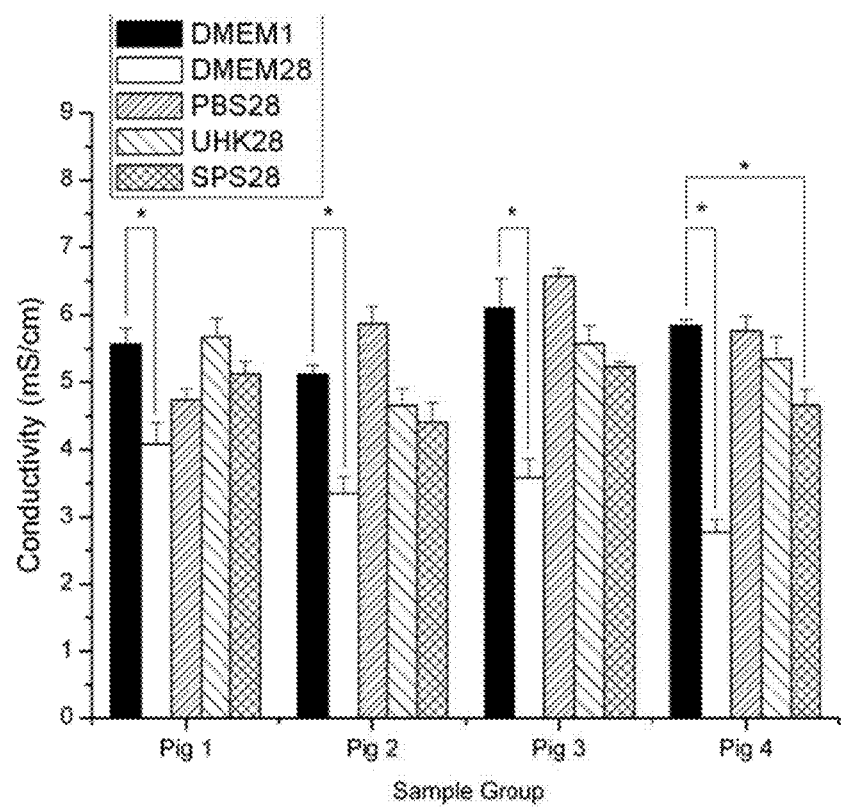
FIG. 3 is a graph illustrating the impact of hypothermic storage on cartilage permeability based on the electrical conductivity of cartilage samples in hypotonic saline.

Based on the data of FIGS. 1 and 2, cartilage permeability was further evaluated in samples stored in the different solutions. The samples stored in DMEM for 28 days (i.e., DMEM 28) exhibited significantly lower conductivity than samples stored in the other solutions (i.e., PBS, UHK, and SPS). FIG. 3 demonstrates the impact of hypothermic storage of cartilage permeability assessed by measuring electrical conductivity in hypotonic saline. The data is expressed as the mean±1 se and * indicates significant differences at p<0.05 between a DMEM control at day one compared with storage groups after 28 days, n=5 samples per porcine donor. The day 28 DMEM group was significantly less in four independent experiments. Thus, these data further demonstrate the correlation between high cell viability and low permeability when cartilage was stored in DMEM.

EXAMPLES

Example 1: Assessing Impact of Matrix Metalloproteinase (MMP) Inhibition on Cartilage Properties During Storage in Extracellular-Type Solution Animal product-free culture medium are formulated with varying concentrations of an MMP inhibitor (e.g., Doxycycline). Biomaterial properties including chondrocyte viability, cartilage chemistry, permeability and other biomaterial properties are compared over hypothermic storage periods of at least one month. Biomaterial testing is performed using established methods [Yao, 2002; Gu, 2004; Brockbank, 2011 (see reference list below)].

Doxycycline is used clinically for the treatment of periodontal disease and is the only MMP inhibitor widely available for clinical use. Doxycycline has been shown to have beneficial in vivo effects on cartilage such as reducing MMP 8, 9, and 13 activity in animal models and humans. Furthermore, in vitro studies suggest that Doxycycline may inhibit MMP synthesis as well as MMP activity.

Additional MMP inhibitors including, for example, TIMPs, PCK3145, a synthetic peptide corresponding to amino acids 31-45 of prostate secretory protein 94, and Marimastat (BB-2516) may also be effective. Both PCK3145 and Marimastat have been well tolerated in early Phase clinical studies. It is also likely that solution exchange at weekly intervals is not needed, however the ratio of cartilage mass to solution volume may need to be explored. High Doxycycline concentrations may be needed for long-term storage without solution exchange.

Experimental Design

Porcine cartilage plugs are obtained, and these plugs are stored at 4° C. (hypothermic conditions) in animal product-free DMEM supplemented with 0 to 300 µM Doxycycline. In certain samples, media is changed weekly, as in prior studies (FIGS. 1-3), and for other samples, media is not changed during storage. These two sample sets (i.e., (1) media changed weekly and (2) no media change) are compared. In certain aspects, it is desirable to minimize the need for handling of allografts once they are placed in storage.

Methods:

Pig knees are procured post-mortem from adult domestic Yorkshire cross-farm pigs (25 Kg). After procuring the knees, the knees are placed in zip lock bags with iodine solution and transported on ice to the lab for aseptic dissection. Femoral head cartilage disc-shaped plugs are prepared using sterile punches. Groups of 5 plugs are placed in storage solution in sterile containers with and without weekly media exchange for 1-2 months.

Metabolic Activity:

A rezasurin reduction assay is used to evaluate the metabolic activity of control and treated cartilage plugs [O'Brien, 2000; Brockbank, 2011]. Tissue plugs (n=5/experiment/donor) are incubated in 2 ml of DMEM+10% FBS culture medium for one hour to equilibrate followed by the addition of 20% resazurin reduction assay solution under standard cell culture conditions for 3 hours. The resazurin reduction assay reagent is a fluorometric indicator based on detection of metabolic activity. The amount of fluorescence is measured in duplicates by the multimode microplate reader at an excitation wavelength of 544 nm and an emission wavelength of 590 nm. This evaluation is performed daily for several days to allow characterization of re-warmed cells in tissues (FIG. 2). Resazurin is not cytotoxic at the concentration employed, so the same tissue samples can be tested on multiple occasions. Results shortly after rewarming (day 0) demonstrate cell viability, after 1-2 days a decrease indicates cell death due to apoptosis, and increases measure cell proliferation. Tissue plugs are then dried to obtain the dry weight. For each experimental group and untreated controls, cell metabolic activity are expressed as relative fluorescence units (RFU) per mg of dry weight or per tissue plug.

Other Viability Assessment Methods:

The metabolic assay described above is the primary viability assessment method; however, additional viability assessment assays may be performed. For example, cell viability can be further determined by fluorescent live/dead staining of cells. The cells can also be assessed after release from tissue plugs by enzyme digestion and assessed using the membrane integrity-based Trypan Blue exclusion assay [Brockbank, 2011]. Cells may also be cultured in DMEM for at least one week to verify that the cells, chondrocytes, are actually able to adhere and proliferate in vitro. Cell counts and digital image analysis may be performed on the cultures.

Water, proteoglycan, and collagen contents: After material property measurements, samples may be lyophilized to determine water (porosity), proteoglycan (S-GAG), and collagen (hydroxyproline) contents. Samples are analyzed for porosity based on Archimedes' principle [Gu, 2004], the S-GAG using a method described by Farndale (1982), and for hydroxyproline content using the method of Bergman and Loxley (1970).

Electrical Conductivity:

Tissue conductivity is measured at zero fluid flow condition using a standard apparatus [Gu 2002a; 2002b] which consists of current and voltage electrodes placed around a Plexiglas chamber containing each specimen. Employing a combination of a 4-wire method and a Keithley Source Meter, the resistance (R) across the specimen is measured at a very low current density of 0.015 mA/cm². A current sensing micrometer is used to measure specimen dimensions, the corresponding electrical conductivity is generated using the following equation:

$$\chi = h/(RA) \tag{1}$$

where A is the cross sectional area, and h is the thickness of the tissue specimen. Electrical conductivity measurements are performed in either isotonic or hypotonic phosphate buffered saline (PBS, pH 7.4) at room temperature (22° C.).

Solute Diffusivity:

Under a zero fluid flow condition, the electrical conductivity ($\chi$) of a tissue in NaCl solution is related to Na⁺ and Cl⁻ diffusivities ($D^\alpha$, $\alpha = +, -$) by Maroudas (1968):

$$\chi = F_c^2 \phi^w (c^+ D^+ + c^- D^-)/RT, \tag{2}$$

where $F_c$ is the Faraday constant, $\phi^W$ is the volume faction of water (porosity), $c^+$ is the cation (Na⁺) concentration, and $c^-$ is the anion (Cl⁻) concentration, R is the gas constant, T is the temperature. The $c^+$ and $c^-$ can be calculated using Donnan equation [Maroudas, 1975]:

$$c^+ = (c^F + \sqrt{(c^F)^2 + 4c^{*2}})/2, c^- = (-c^F + \sqrt{(c^F)^2 + 4c^{*2}})/2 \tag{3}$$

Here $c^F$ is the tissue fixed charge density (FCD) and $c^*$ is the NaCl concentration of the bathing solution. The tissue FCD is determined from the measured proteoglycan content. Using the data of the electrical conductivity, FCD, porosity, and the concentration of the bathing solution, the ion diffusivities can be calculated from equation 3. This method can be used for studying porcine and bovine cartilage tissues [Gu, 2004; Jackson, 2006].

Figure 4:
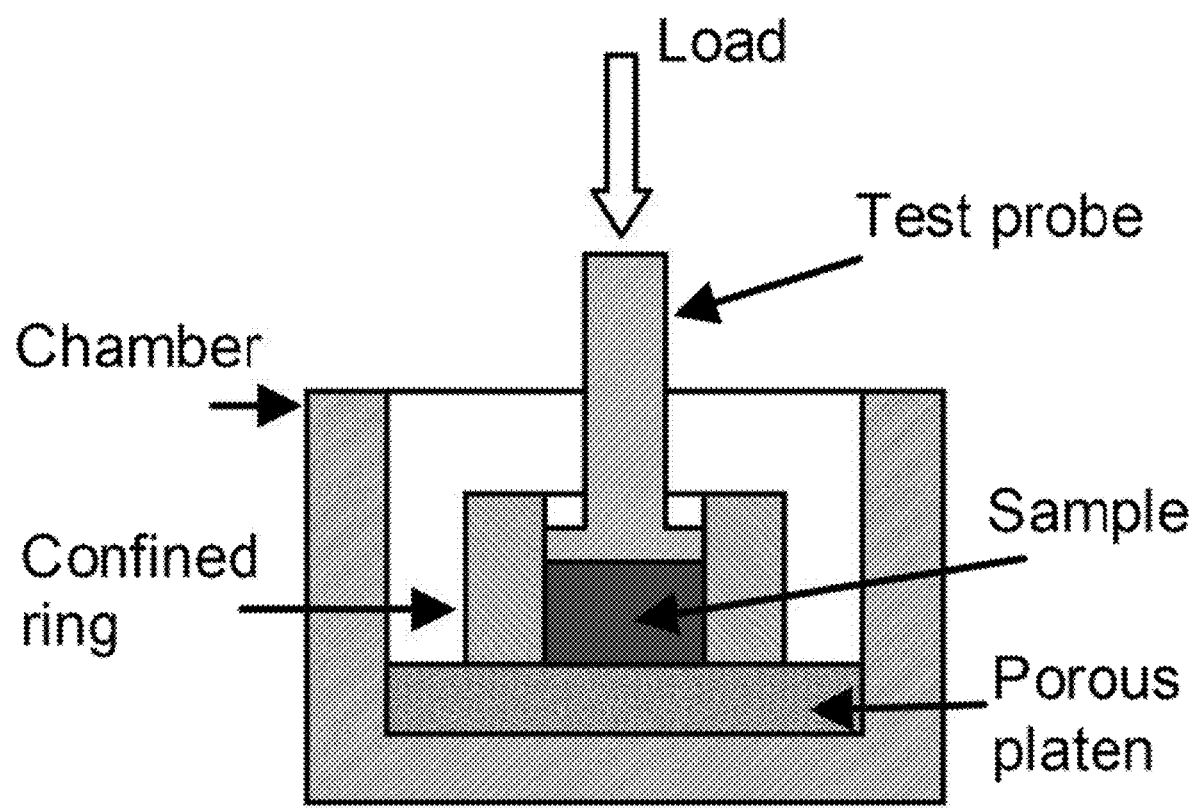
FIG. 4 is a schematic representation of a compression chamber used to quantify mechanical properties (e.g., creep compression) of cartilage.

Compressive Aggregate Modulus and Hydraulic Permeability:

The mechanical properties of the cartilage samples are determined using confined compression creep test. The test is applied in the load bearing axial direction on a Dynamic Mechanical Analyzer (Q800, TA Instruments, New Castle, DE). The specimen is allowed to equilibrate in PBS at its initial height measured under a minute compressive tare load in a confined chamber (FIG. 4). After equilibrium, the swelling stress is recorded at the initial height and the specimen is subjected to a constant compressive stress for three hours. Creep data is curve-fitted to the biphasic theory to obtain the aggregate modulus $H_A$ and hydraulic permeability [Yao, 2002].

Experimental Data

Figure 5:
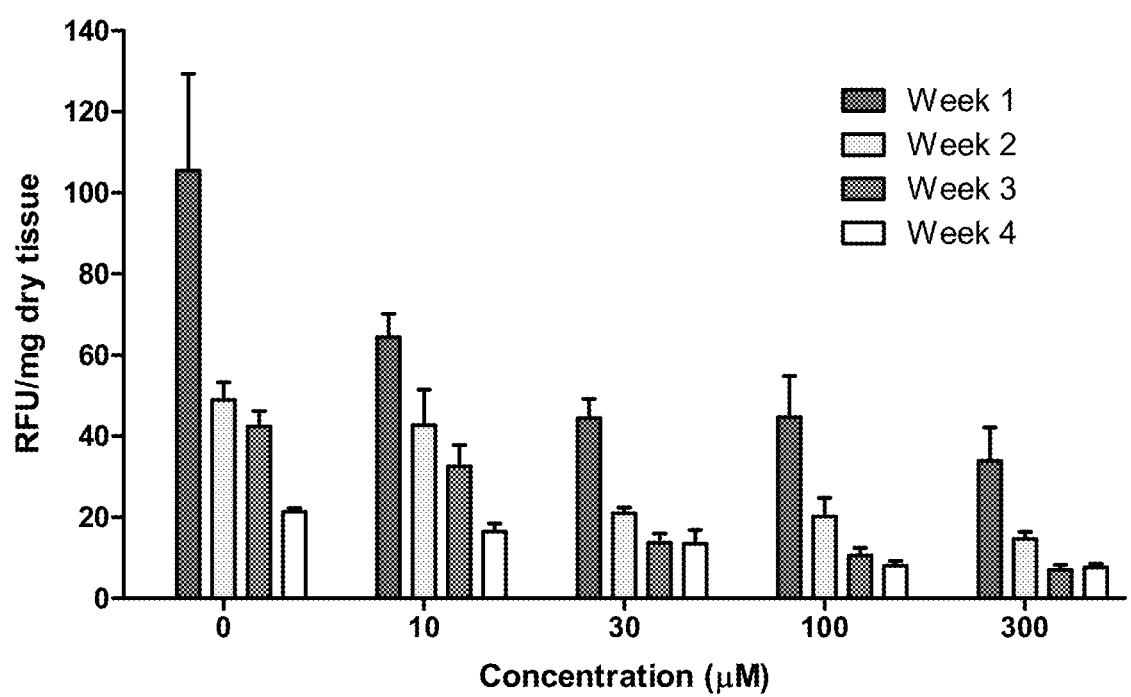
FIG. 5 is a graph showing the impact of doxycycline concentration on cartilage cell viability after various storage intervals.
Figure 6:
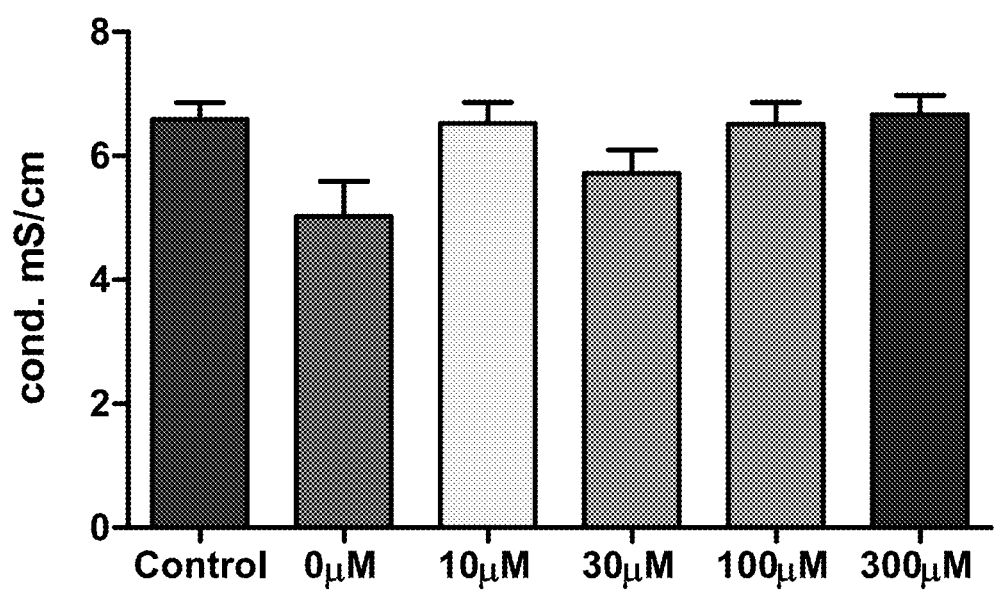
FIG. 6 is a graph showing the impact on porcine cartilage plug electrical conductivity after one month of refrigerated storage in various concentrations of doxycycline.

In a cold storage experiment using the methods described immediately above in Example 1, 45 pieces of pig cartilage plugs were harvested from one pig. 20 pieces of cartilage plugs were included in the viability test (FIG. 5). In this viability test, 4 plugs were used per Doxycycline concentration. Another 25 plugs were used for mechanical test (FIG. 6).

For the data shown in FIG. 5, each plug diameter was 6 mm. An injectable form of Doxycycline (DOXY 100™) was obtained from APP Pharmaceuticals, LLC, (Schaumberg, IL) with a molecular weight of 1,025.89 daltons. The storage solutions contained DMEM, 1.44 mg/ml ascorbic acid, manitol 0.9 mg/ml, and different concentrations of doxycycline (OuM, 10 uM, 30 uM, 100 uM, 300 uM). The storage temperature was 4° C. As shown in FIG. 5, the viability tests were tracked from week 0 to week 4. As shown in FIG. 6, the mechanical test was only performed at week 4.

Viability Assessment:

Chondrocyte metabolic activity was assessed using the resazurin reduction method. The resazurin reduction assay, commonly known as the alamarBlue assay, incorporates a water soluble fluorometric viability oxidation-reduction (REDOX) indicator which detects metabolic activity by both fluorescing and changing color in response to chemical reduction of the growth medium. Metabolically active cells reduce resazurin to fluorescing resorufin. Fresh control and hypothermically stored tissue samples were placed in 37° C. culture conditions for 1 hour to permit adjustment to tissue culture conditions in DMEM plus 10% FBS. The tissues were then incubated for three hours with resazurin working solution, after which aliquots of medium were placed in microtiter plate wells and read on a microtiter plate spectrofluorometer at a wavelength of 590 nm. The data is expressed as the mean±1 se relative fluorescent units.

Biomaterial Testing:

Cartilage plugs were also evaluated for permeability by measuring their electrical conductivity to determine if cartilage matrix characteristics were being altered during storage. Specimens were prepared by cutting a 5 mm cylindrical plug using a corneal trephine from the stored 6 mm diameter cartilage discs. The samples were tested after 0 and 1 month of storage, the cartilage surfaces were trimmed manually using a sharp blade. Then conductivity was tested in hypotonic saline. The height of each specimen was measured with an electrical current sensing micrometer. All electrical conductivity measurements were performed in hypotonic saline at room temperature (22° C.). Electrical conductivity is a material property of biological tissues. Its value is related to the diffusivity of small ions inside the tissue, which depend on tissue composition and structure.

Statistical Methods:

One-way ANOVA ($p<0.05$ being considered significant) was conducted to determine differences in mean values of cell fluorescence units and electrical conductivity.

The viability was impacted by the presence of doxycycline in a dose dependent manner. As shown in FIG. 5, the zero group (i.e., the group having no doxycycline added) was significantly higher than all treatment groups at all time points ($p<0.05$). As further shown in FIG. 5, the 10 μM group was significantly higher than all other groups from week 2-4 (FIG. 5; $p<0.05$). This data is expressed as the mean±1 standard error of the mean, n=4 using one way analysis of variance (ANOVA).

As shown in FIG. 6, the electrical conductivity was lower in the 0 μM group at one month and all doxycycline groups (i.e., 10 μM, 30 μM, 100 μM, and 300 μM) were similar to the time zero group (FIG. 6; $p<0.05$). This data is expressed as the mean±1 standard error of the mean, n=5 using one way analysis of variance (ANOVA).

The results of this experiment with doxycycline demonstrate that inhibition of MMPs promote retention of electrical conductivity and permeability, in the presence of viable cells. For example, this is demonstrated by the 10 μM group viability (FIG. 5) and conductivity results (FIG. 6).

Example 2: Determining Impact of Key Culture Medium Components on Cartilage Stored in an Intracellular-Type Hypothermic Solution Step I: Animal product-free hypothermic storage solution is formulated with and without the primary nutrients in Dulbecco's Modified Eagle Medium (DMEM). Step II: Various concentrations of Doxycycline are added to the new intracellular-type storage formulation of Example 2 to minimize MMP activity.

Experimental Design

Step I: A nutrient cocktail based upon the DMEM formulation is added to Belzer's solution, the lead clinical organ preservation formulation marketed as SPS-1 (Organ Recovery Systems, Itasca, IL). The nutrient cocktail consists of D-glucose and amino acids (glycine, L-arginine hydrochloride, L-cystine 2HCl, L-glutamine, L-histidine hydrochloride-H2O, L-isoleucine, L-leucine, L-lysine hydrochloride, L-methionine, L-phenylalanine, L-serine, L-threonine, L-tryptophan, L-tyrosine disodium salt dehydrate and L-valine) at concentrations used for DMEM (Mediatech, Manassas, VA, Cat #10-014-CM). The modified formulation is compared with the original formulation. Step II: 0-300 μM Doxycycline is added to the modified Belzer's solution. Cell viability, biomaterial properties, and cartilage biochemistry is performed on cartilage plugs over a period of at least one month of hypothermic storage. The best Doxycycline dose is selected for comparison with the optimized extracellular solution from Example 1. Solution change schedule is also assessed as described in Example 1.

Belzer's solution (SPS-1) and Doxycycline are selected because they are FDA cleared products. Step I: The higher viability values obtained employing DMEM in the preliminary data (FIG. 2) is most likely due to nutritional components supporting the low level of metabolism (<10%) anticipated at 4° C. during hypothermic storage. Step II: This step may be useful because increased MMP synthesis can occur when chondrocyte viability is improved by nutrient supplementation in Step I.

Example 3: Comparing of Extracellular-Type and Intracellular-Type Solutions

Experimental Design

Cartilage plug properties are assessed after storage in the extracellular-type and intracellular-type preservation formulations described in Example 1 and Example 2. Plugs are evaluated over a period of 2 months (e.g., time 0 and after 1, 4 and 8 weeks of storage) and gene expression is assessed in addition to the assays used in the earlier examples. Two samples are assessed at each time point for each group and the experiment is repeated four times (7 groups×2 replicates×4 experiments=56 samples).

The purpose of this example is to compare the extracellular-type solution of Example 1 with the intracellular-type solution of Example 2. In addition to the cell viability and ECM assays described above, analysis of gene expression is conducted to ensure that the chondrocytes are expressing appropriate pro-cartilage genes relative to chondrocytes in fresh untreated cartilage.

Methods:

Gene Expression:

Samples are snap frozen in liquid nitrogen and stored at −80° C. Total cellular RNA is isolated (RNeasy Kit, Qiagen, CA), reverse-transcribed into cDNA (Omniscript RT kit, Qiagen, CA), evaluated for quality and changes in gene expression due to storage is quantified using real time PCR. Retention of phenotype (and/or loss of phenotype) is assessed by evaluating expression of Sox9, aggrecan, collagen type II (versus dedifferentiation marker collagen type I), cartilage oligomeric matrix, ECM resorption marker (MMP-9) plus protein and hypertrophic marker genes (collagen type 10 and alkaline phosphatase).

Unless defined otherwise, all technical and scientific terms used herein have the same meanings as commonly understood by one of skill in the art to which the disclosed invention belongs.

Those skilled in the art will recognize, or be able to ascertain using no more than routine experimentation, many equivalents to the specific embodiments of the invention described herein. Such equivalents are intended to be encompassed by the claims.

REFERENCES

Citations in the following list of references are incorporated in pertinent part by reference herein for at least the reasons cited in the text.

Allen R T, Robertson C M, Pennock A T, Bugbee W D, Harwood F L, Wong V W, Chen A C, Sah R L, Amiel D: Analysis of stored osteochondral allografts at the time of surgical implantation. Am J Sports Med 2005; 33:1479-1484. American Academy of Orthopaedic Surgeons; *The Burden of Musculoskeletal Diseases in the United States*. Rosemont, IL: United States Bone and Joint Decade, 2008. Bakay A, Csonge L, Papp G, Fekete L: Osteochondral resurfacing of the knee joint with allograft: clinical analysis of 33 cases. Int Orthop 1998; 22:277-281. Ball S T, Amiel D, Williams S K, Tontz W, Chen A C, Sah R L, Bugbee W D: The effects of storage on fresh human osteochondral allografts. Clin Orthop Relat Res 2004; 418:246-252. Beaver R J, Mahomed M, Backstein D, Davis A, Zukor D J, Gross A E: Fresh osteochondral allografts for post-traumatic defects in the knee: a survivorship analysis. J Bone Joint Surg Br 1992; 74:105-110. Bergman I, Loxley R. New spectrophotometric method for the determination of proline in tissue hydrolyzates. Anal Chem 1970; 42 702-6. Black J, Shadle C A, Parsons J R, Brighton C T: Articular cartilage preservation and storage. II. Mechanical indentation testing of viable, stored articular cartilage. Arthritis Rheum 1979; 22:1102-1108. Bowyer J, Chris G Heapy, Joanne K Flannelly, John C Waterton, Rose A Maciewicz. Evaluation of a magnetic resonance biomarker of osteoarthritis disease progression: doxycycline slows tibial cartilage loss in the Dunkin Hartley guinea pig. Int J Exp Pathol. 2009 April; 90(2): 174-181. Brockbank, K. G. M., Chen, Zhen Z., Song, Ying, C. (2010) Vitrification of Porcine Articular Cartilage. Cryobiology 60, 217-221. http://www.pubmedcentral.gov/articlerender.fcgi?artid=2834839 Brockbank K G M, MacLellan W R, Xie J, Hamm-Alvarez S F, Chen Z Z, Schenke-Layland K: Quantitative second harmonic generation imaging of cartilage damage. Cell Tissue Bank 2008; 9:299-308. Brockbank K G M, Rahn E, Wright G J, Chen Z, Yao H: Impact of hypothermia upon chondrocyte viability and cartilage matrix permeability after 1 month of refrigerated storage. Transfus Med Hemother 2011; 38:387-293. Brockbank K G M, Taylor M J: Tissue Preservation; in: Baust J G, Baust J M (eds): Advances in Biopreservation. Boca Raton, FL, CRC Press/Taylor & Francis, 2007, 8, pp 157-196. CDC website—www.cdc.gov/arthritis/data_statistics/arthritis_related_stats.htm. Farndale R W, Sayers C A, Barrett A J. A direct spectrophotometric microassay for sulfated glycosaminoglycans in cartilage cultures. Connect Tissue Res 1982; 9 247-8. Foresight study performed on Hypothermic Tissue Storage and Transport Solution by Foresight Science & Technology for Cell & Tissue Systems, Inc. Gross A E, Ont, O, Kim W, Las Heras F, Backstein D, Safir O, Pritzker M D, KPH: Fresh osteochondral allografts for posttraumatic knee defects: Long-term followup. Clin Orthop Relat Res 2008; 466:1863-1870. Gu W Y Justiz M A. Apparatus for measuring the swelling dependent electrical conductivity of charged hydrated soft tissues. J Biomech Eng 2002a; 124:790-3. Gu W Y Justiz M A, Yao H. Electrical conductivity of lumbar annulus fibrosis: Effects of porosity and fixed charge density. Spine 2002b; 27:2390-5. Gu W Y and Yao H, Effects of hydration and fixed charged density on fluid transport in charged hydrated soft tissues, Annals of Biomedical Engineering, 2003; 31, 1162-1170. Gu W Y, Yao H, Vega A L et al. Diffusivity of ion in agarose gels and intervertebral disc: Effect of porosity. Ann Biomed Eng 2004; 32(12):1710-7. Hanemaaijer R, Visser H, Koolwijk P, Sorsa T, Salo T, Golub L M, van Hinsbergh V W. Inhibition of MMP synthesis by doxycycline and chemically modified tetracyclines (CMTs) in human endothelial cells. Adv Dent Res. 1998 November; 12(2):114-8. Jackson A, Yao H, Brown M et al. Anisotropic ion diffusivity in intervertebral discs: An electrical conductivity approach. Spine 2006; 31(24):2783-89. Kim W, Vacanti J P, Mooney D, Upton J, Ibarra C, Vacanti C A: Functional viability of chondrocytes stored at 4 degrees C. Tissue Eng 1996; 2:75-81. LaPrade R F, Botker J, Herzog M, Agel J: Refrigerated osteoarticular allografts to treat articular cartilage defects of the femoral condyles. A prospective outcomes study. J Bone Joint Surg Am 2009; 91:805-811. Malinin T, Temple H T, Buck B E: Transplantation of osteochondral allografts after cold storage. J Bone Joint Surg Am 2006; 88:762-770. Maroudas A: Physicochemical properties of cartilage in the light of ion exchange theory. Biophys J 1968; 8:575-595. Maroudas A. Biophysical chemistry of cartilaginous tissues with special reference to solute and fluid transport. Biorheology 1975; 12 233-48. Oates K M, Chen A C, Young E P, Kwan M K, Amiel D, Convery F R: Effect of tissue culture storage on the in vivo survival of canine osteochondral allografts. J Orthop Res 1995; 13:562-569. O'Brien J, Wilson I, Orton T, Pognan F: Investigation of the alamar blue (resazurin) fluorescent dye for the assessment of mammalian cell cytotoxicity. Eur J Biochem 2000; 267:5421-5426. Onuma K, Urabe K, Naruse K, Park H J, Uchida K, Itoman M: Cold preservation of rat osteochondral tissues in two types of solid organ preservation solution, culture medium and saline. Cell Tissue Bank 2009; 10:1-9. Rodrigo J, Thompson E, Travis C: 4 degree C. preservation of avascular osteocartilaginous shell allografts in rats. Trans Orthop Res Soc 1980; 5:72. Rohde R S, Studer R K, Chu C R: Mini-pig fresh osteochondral allografts deteriorate after 1 week of cold storage. Clin Orthop Relat Res 2004; 427:226-233. Smith G. N. Jr, Yu L. P. Jr, Brandt K. D., Capello W. N. (1998) Oral administration of doxycycline reduces collagenase and gelatinase activities in extracts of human osteoarthritic cartilage. J. Rheumatol. 25, 532-535. Song Y C, An Y H, Kang Q K, Li C, Boggs J M, Chen Z Z, Taylor M J, Brockbank K G M. Vitreous preservation of articular cartilage grafts. *Journal of Investigative Surgery.* 2004; 17:65-70. Song Y C, Lightfoot F G, Chen Z, Taylor M J, Brockbank K G M. Vitreous preservation of rabbit articular cartilage. *Cell Preservation Technology.* 2004; 2(1):67-74. Stone B B, Defranzo B E, Dicesare C, et al. Cryopreservation of human articular cartilage for autologous chondrocyte transplantation. *Cryobiology.* 1998; 37:445-446. (abstract). Taylor M J: Biology of cell survival in the cold: The Basis for Biopreservation of Tissues and Organs. In: Baust J G, Baust J M, editors. Advances in Biopreservation. Boca Raton: CRC Press; 2007: pp 15-62. Teng M S, Yuen A S, Kim H T: Enhancing osteochondral allograft viability: effects of storage media composition. Clin Orthop Relat Res 2008; 466:1804-1809. Tomford W W, Fredericks G R, Mankin H J. Studies on cryopreservation of articular cartilage chondrocytes. *J Bone Joint Surg Am.* 1984; 66:253-259. Wang Y, *Bella* E, Lee C S, Migliaresi C, Pelcastre L, Schwartz Z, Boyan B D, Motta A. The synergistic effects of 3-D porous silk fibroin matrix scaffold properties and hydrodynamic environment in cartilage tissue regeneration. Biomaterials. 2010; 31(17): 4672-81. PMID 20303584. Wayne J S, Amiel D, Kwan M K, Woo S L, Fierer A, Meyers M H: Long-term storage effects on canine osteochondral allografts. Acta Orthop Scand 1990; 61:539-545. Williams S K, Amiel D, Ball S T, Allen R T, Wong V W, Chen A C, Sah R L, Bugbee W D: Prolonged storage effects on the articular cartilage of fresh human osteochondral allografts. J Bone Joint Surg Am 2003; 85:2111-2120. Williams R J 3rd, Dreese J C, Chen C T: Chondrocyte survival and material properties of hypothermically stored cartilage: an evaluation of tissue used for osteochondral allograft transplantation. Am J Sports Med. 2004; 32:132-139. Worldwide markets and emerging technologies for tissue engineering and regenerative medicine. InteLab Corporation, Marketing and Technology Reports. January, 2009. Yao H, Justiz M A, Flagler D et al. Effects of swelling pressure and hydraulic permeability on dynamic compressive behavior of lumbar annulus fibrosus. Ann Biomed Eng 2002; 30:1234-41.

What is claimed is:

1. A method for storing a biomaterial comprising:
preparing a composition by placing a biomaterial in a solution that includes at least one agent that reduces or prevents a loss of biomaterial properties, the biomaterial properties comprising cell viability and extracellular matrix integrity, the extracellular matrix integrity including extracellular matrix permeability;
after formation of the composition, adjusting the solution comprising the biomaterial to a hypothermic temperature; and
then reducing or preventing the loss of the cell viability and the extracellular matrix permeability by storing the biomaterial in the solution at a hypothermic temperature ranging from 0° C. to +5° C. for a storage period of hours to 1 month,
wherein the solution is an animal product-free solution, the biomaterial comprises chondrocytes in an extracellular matrix or cartilage, and
the at least one agent comprises doxycycline having a concentration ranging from 10 µM to 30 µM.

2. The method of claim 1, wherein the composition includes at least one additive that promotes retention of extracellular matrix integrity and cell viability, the at least one additive comprising an amino acid, a plurality of amino acids, a sugar, a plurality of sugars, a lipid, a plurality of lipids, a vitamin, a plurality of vitamins, or any combination thereof.

3. The method of claim 1, wherein the hypothermic temperature in the adjusting step ranges from −25° C. to +35° C.

4. The method of claim 1, wherein the hypothermic temperature in the adjusting step ranges from 0° C. to +10° C.

5. A method for storing a biomaterial comprising:
preparing a composition by placing a biomaterial in a solution that includes at least one agent that reduces or prevents a loss of biomaterial properties, the biomaterial properties comprising cell viability and extracellular matrix integrity, the extracellular matrix integrity including extracellular matrix permeability;
after formation of the composition, adjusting a temperature of the solution comprising the biomaterial to a hypothermic temperature ranging from 0° C. to +5° C.; and
then reducing or preventing the loss of the cell viability and the extracellular matrix permeability by storing the biomaterial in the solution at a hypothermic temperature ranging from 0° C. to +5° C. for a storage period of hours to 1 month,
wherein the solution is an animal product-free solution, the biomaterial comprises chondrocytes in an extracellular matrix or cartilage, and
the at least one agent comprises doxycycline having a concentration ranging from 10 µM to 30 µM.

6. The method of claim 1, wherein the solution includes Dulbecco's Modified Eagle Medium (DMEM),
the biomaterial is a viable biomaterial that comprises viable cells of chondrocytes in the extracellular matrix or cartilage, and
the at least one agent is 10 µM doxycycline.

7. The method of claim 1, wherein the solution is replaced only once a week during the storage period and until the stored biomaterial is removed from storage.

8. The method of claim 3, wherein the solution is replaced only once a week during the storage period and until the stored biomaterial is removed from storage.

9. The method of claim 6, wherein the solution is replaced only once a week during the storage period and until the stored biomaterial is removed from storage.

10. A method for storing a biomaterial comprising:
preparing a composition by placing a biomaterial in a solution that includes at least one agent that reduces or prevents a loss of biomaterial properties, the biomaterial properties comprising cell viability and extracellular matrix integrity, the extracellular matrix integrity including extracellular matrix permeability;
after formation of the composition, adjusting a temperature of the solution comprising the biomaterial to a hypothermic temperature ranging from −25° C. to +10° C.; and
then reducing or preventing the loss of the cell viability and the extracellular matrix permeability by storing the biomaterial in the solution at a hypothermic temperature ranging from 0° C. to +5° C. for a storage period of hours to 1 month, wherein the solution is an animal product-free solution,
the biomaterial comprises chondrocytes in an extracellular matrix or cartilage, and
the at least one agent comprises doxycycline having a concentration ranging from 10 μM to 30 μM.

* * * * *